(12) United States Patent
Straub et al.

(10) Patent No.: US 8,900,257 B2
(45) Date of Patent: Dec. 2, 2014

(54) CATHETER COMPRISING A PROTECTION SYSTEM FOR ASPIRATING, FRAGMENTING AND EXTRACTING REMOVABLE MATERIAL FROM HOLLOW BODIES OR VESSELS OF A HUMAN OR ANIMAL BODY

(75) Inventors: Immanuel Straub, Wangs (CH); Mathias Heller, Elsau (CH)

(73) Assignee: Straub Medical AG, Wangs (CH)

( * ) Notice: Subject to any disclaimer, the term of this patent is extended or adjusted under 35 U.S.C. 154(b) by 287 days.

(21) Appl. No.: 13/405,349

(22) Filed: Feb. 26, 2012

(65) Prior Publication Data

US 2012/0179181 A1   Jul. 12, 2012

Related U.S. Application Data

(63) Continuation-in-part of application No. PCT/IB2010/053816, filed on Aug. 25, 2010.

(30) Foreign Application Priority Data

Aug. 27, 2009  (CH) ...................................... 1328/09

(51) Int. Cl.
| | |
|---|---|
| *A61B 17/22* | (2006.01) |
| *A61B 17/3207* | (2006.01) |
| *A61F 2/01* | (2006.01) |
| *A61B 19/00* | (2006.01) |
| *A61B 17/221* | (2006.01) |
| *A61B 17/00* | (2006.01) |

(52) U.S. Cl.
CPC ......... *A61B 17/320758* (2013.01); *A61F 2/013* (2013.01); *A61B 2019/481* (2013.01); *A61B 2017/2215* (2013.01); *A61B 17/320783* (2013.01); *A61B 2017/00685* (2013.01)
USPC ........................................... 606/159; 604/22

(58) Field of Classification Search
USPC ......... 606/127, 128, 159, 167, 168, 170, 180, 606/200; 604/22, 35, 264, 523, 526; 600/564, 565, 568
See application file for complete search history.

(56) References Cited

U.S. PATENT DOCUMENTS

| 2,026,630 A | 1/1936 | Harris |
|---|---|---|
| 3,082,805 A | 3/1963 | Royce |

(Continued)

FOREIGN PATENT DOCUMENTS

| DE | 10162933 A1 | 7/2003 |
|---|---|---|
| EP | 0310285 A2 | 4/1989 |

(Continued)

OTHER PUBLICATIONS

English translation of the Written Opinion of the International Search Authority for parent International Application No. PCT/IB2010/053816.

(Continued)

*Primary Examiner* — Dianne Dornbusch
*Assistant Examiner* — Robert Lynch
(74) *Attorney, Agent, or Firm* — Matthew B. Dernier, Esq; Gibson & Dernier LLP (57) ABSTRACT

Systems, devices, and processes for aspirating, fragmenting and extracting removable material from hollow bodies. A guide wire (11) is inserted into the hollow body (1) via an opening. Material is removed by means of a reducing catheter (3) having a working head (6) with stator (8) and rotor (9) that is connected to a feed screw (10). The stator (8) has a lateral inlet opening (8*a*) which is formed as two circular holes arranged in axial succession. Material forced into the inlet openings (8*a*) is sheared and/or fragmented. A flexible sleeve (7) serves to discharge the ablated material. Prior to this, a sheathing catheter (4) is inserted into the hollow body (1) until in front of the material to be removed. The cross-section of the hollow body (1) is occluded by the sheathing catheter (4), preventing detached fragments from being accidentally washed away.

5 Claims, 7 Drawing Sheets

(56) References Cited

U.S. PATENT DOCUMENTS

| | | |
|---|---|---|
| 3,732,858 A | 5/1973 | Banko |
| 3,945,375 A | 3/1976 | Banko |
| 4,705,511 A | 11/1987 | Kocak |
| 4,844,064 A | 7/1989 | Thimsen et al. |
| 4,857,046 A | 8/1989 | Stevens et al. |
| 4,867,157 A | 9/1989 | McGurk-Burleson et al. |
| 4,935,025 A | 6/1990 | Bundy et al. |
| 5,078,723 A | 1/1992 | Dance et al. |
| 5,084,052 A | 1/1992 | Jacobs |
| 5,100,426 A | 3/1992 | Nixon |
| 5,102,415 A | 4/1992 | Guenther et al. |
| 5,226,909 A | 7/1993 | Evans et al. |
| 5,312,425 A | 5/1994 | Evans et al. |
| 5,417,703 A | 5/1995 | Brown et al. |
| 5,569,178 A | 10/1996 | Henley |
| 5,571,122 A | 11/1996 | Kelly et al. |
| 5,695,519 A | 12/1997 | Summers et al. |
| 5,833,704 A | 11/1998 | McCombs et al. |
| 5,873,882 A | 2/1999 | Straub et al. |
| 5,876,414 A | 3/1999 | Straub |
| 6,217,565 B1 | 4/2001 | Cohen |
| 6,454,775 B1 | 9/2002 | Demarais et al. |
| 6,565,588 B1 | 5/2003 | Clement et al. |
| 6,579,298 B1 | 6/2003 | Wyzgala et al. |
| 6,660,014 B2 | 12/2003 | Demarais et al. |
| 6,682,543 B2 | 1/2004 | Barbut et al. |
| 6,702,830 B1 | 3/2004 | Demarais et al. |
| 6,945,977 B2 | 9/2005 | Demarais et al. |
| 7,485,125 B2 | 2/2009 | Sjostrom |
| 7,905,896 B2 | 3/2011 | Straub |
| 8,114,106 B2 | 2/2012 | Straub |
| 2002/0010487 A1 | 1/2002 | Evans et al. |
| 2002/0123761 A1 | 9/2002 | Barbut et al. |
| 2003/0055404 A1 | 3/2003 | Moutafis |
| 2003/0114875 A1 | 6/2003 | Sjostrom |
| 2007/0219484 A1 | 9/2007 | Straub |
| 2008/0004646 A1 | 1/2008 | To et al. |

FOREIGN PATENT DOCUMENTS

| | | |
|---|---|---|
| EP | 0448859 A2 | 10/1991 |
| EP | 0448859 A3 | 5/1992 |
| EP | 0267539 B1 | 4/1993 |
| EP | 0582533 A1 | 2/1994 |
| EP | 0669106 A1 | 8/1995 |
| EP | 0680730 A2 | 11/1995 |
| EP | 0680730 A3 | 1/1996 |
| EP | 0739603 A1 | 10/1996 |
| EP | 0669106 B1 | 2/1999 |
| EP | 0739603 B1 | 8/2001 |
| EP | 1690504 A1 | 8/2006 |
| JP | H05-78207 U | 10/1993 |
| JP | H10-277047 A | 10/1998 |
| WO | 91/01114 A | 2/1991 |
| WO | 94/24941 A1 | 11/1994 |
| WO | 96/29941 A1 | 10/1996 |
| WO | 00/47116 A1 | 8/2000 |
| WO | 00/54659 A1 | 9/2000 |
| WO | 02/49690 A2 | 6/2002 |
| WO | 02/049690 A3 | 9/2002 |
| WO | 2005/084562 A2 | 9/2005 |
| WO | 2005/084562 A3 | 8/2007 |
| WO | 2010/061308 A1 | 6/2010 |

OTHER PUBLICATIONS

File history of commonly-owned copending U.S. Appl. No. 13/129,951, filed May 18, 2011.

Printout of Internet description of "Fogarty Arterial Embolectomy Catheter," 1 page at address www.edwards.com/products/vascular/clotmanagement/EmbolectomyCatheter.htm, retrieved on Feb. 24, 2009; in English.

CATHETER COMPRISING A PROTECTION SYSTEM FOR ASPIRATING, FRAGMENTING AND EXTRACTING REMOVABLE MATERIAL FROM HOLLOW BODIES OR VESSELS OF A HUMAN OR ANIMAL BODY

This application is a Continuation-In-Part (CIP) of copending PCT International application no. PCT/IB2010/053816 filed on Aug. 25, 2010 and published as WO2011/024124A1 on Mar. 3, 2011, which in turn claims benefit of priority to prior Swiss national application CH 1328/09 filed on Aug. 27, 2009; the entirety of parent PCT International application no. PCT/IB2010/053816 is hereby expressly incorporated herein by reference, in its entirety and as to all its parts, for all intents and purposes, as if set forth identically in full herein.

The invention relates to a device for removing and extracting removable material, such as deposits from inside hollow bodies, in particular for removing and extracting thrombi and emboli from blood vessels, said device comprising a reducing catheter which can be inserted into the hollow body, and a sheathing catheter which can likewise be inserted into the hollow body, wherein the reducing catheter and the sheathing catheter each have a proximal end and a distal end, the sheathing catheter being connected at its distal end region to a radially deformable, funnel-shaped end piece which is made of liquid-permeable material and widens in cross-section towards its free, distal end, and the reducing catheter comprises a working head and a flexible sleeve connected thereto, wherein the working head of the reducing catheter has an outer diameter which is smaller than the inner diameter of the widened end piece for insertion into the region of the funnel-shaped end piece of the sheathing catheter. The invention also relates to a reducing catheter for a device of this type and to a method for removing and extracting removable material from inside hollow bodies.

Deposits, for example in the form of thrombi and emboli in blood vessels, reduce the sectional area of flow of hollow bodies, such as blood vessels, arteries and veins. This can lead to congestion or to a total blockage (emboli) of the blood vessel. The health consequences may be circulatory disorders or, in extreme cases, the failure of extremities or even vital organs.

In particular, hollow bodies are also understood to mean: bypasses, stents or the like, but also hollow organs, such as the bladder, kidneys, lungs, heart and uterus.

A catheter, in particular for removing fresh blood clots is known from WO2005/084562A, said catheter having a working head comprising a stator and a rotor rotating therein and connected to a feed screw. The trade name of this catheter is Aspirex® (applicant's trademark). The stator is provided over its circumference with at least one inlet opening. The deposits to be ablated are aspirated into the stator through the inlet openings as a result of the vacuum produced by the feed screw, said deposits being fragmented in the stator between the stator and the feed screw as a result of the shearing action, and lastly being discharged by the feed screw. Particularly in the case of inhomogeneous deposits, it may be that individual particles are washed away with the blood flow, and new congestions may develop at more distant locations, where the vessel lumen are smaller.

U.S. Pat. No. 5,102,415 presents a device for mechanically removing blood clots from veins and arteries. An outer catheter is first inserted into the blood vessel via a guide wire until in front of the thrombus. A sheathing catheter is then inserted through the outer catheter. The sheathing catheter is provided with a radially expandable end piece on its distal end. When the sheathing catheter is inserted into the outer catheter, the end piece is reduced to the inner diameter of the outer catheter. Once the end piece has been pushed through the outer catheter, the end piece unfolds in a funnel-shaped manner. An inner catheter is then inserted through the sheathing catheter and through the thrombus. A miniature balloon is located on the proximal end of the inner catheter. Once the inner catheter has penetrated the thrombus to be removed, the miniature balloon is inflated. By withdrawing the inner catheter, the thrombus is then drawn mechanically into the funnel-shaped end piece. The thrombus is then removed from the blood vessel by extracting the outer catheter together with the sheathing catheter and the inner catheter. This method has the disadvantage that any residues of the thrombus remain attached to the vessel wall and may again form flow obstacles and/or may later be washed away. Residues which are washed away may lead to new blockages in distal, narrow blood vessels.

An apparatus for removing blood clots is known from U.S. Pat. No. 6,454,775 and comprises a flexible catheter and a motor-driven drive unit. A radially expandable working head comprising resilient wires is located on the distal end of the catheter. The deposits are to be detached and removed by rotation of the working head.

In FIG. 9, U.S. Pat. No. 6,454,775 shows a second catheter which is introduced into the blocked blood vessel from the opposite side. This second catheter is provided with a radially expandable funnel-shaped end piece on its distal end. The deposits detached by means of the working head and washed away with the blood flow are caught in the funnel-shaped end piece and then aspirated by the drive unit.

The removal of thrombi by means of this system is relatively complex, since the removed deposits consist of larger and smaller fragments which tend to stick together, but cannot be comminuted, and therefore the particles remaining in the blood can float in the blood. This leads to the formation of clumps and to blocking of the vein system.

A device for removing and extracting deposits from inside hollow bodies is known from U.S. Pat. No. 6,579,298 and comprises a reducing catheter which can be inserted into the hollow body, and a sheathing catheter which can likewise be inserted into the same hollow body. The reducing catheter and the sheathing catheter each have a proximal end and a distal end. The sheathing catheter is connected at its distal end to a radially deformable, funnel-shaped end piece which is made of liquid-permeable material and widens in cross-section towards its distal end. The reducing catheter has a working head and a flexible sleeve connected thereto, wherein the working head of the reducing catheter has an outer diameter which is smaller than the inner diameter of the widened end piece for insertion into the region of the funnel-shaped end piece of the sheathing catheter. The working head of the reducing catheter is formed as a milling cutter.

To remove and extract deposits from inside hollow bodies, the reducing catheter and sheathing catheter are inserted into the hollow body simultaneously in the device according to U.S. Pat. No. 6,579,298 until in front of the material to be removed. The funnel-shaped end piece of the sheathing catheter is then expanded, whereby the hollow body is occluded at least in part. The deposit is then reduced in the hollow body by means of the milling cutter, the material reduced by the milling cutter being sucked up through the flexible sleeve.

The milling cutter merely comminutes the deposits into pieces of undefined size. Pieces of the material to be removed may thus accumulate, which can block the flexible sleeve and thus the removal of the deposits.

The invention presents a system and devices which permit quick and reliable removal of thrombi from blood vessels, but which can also reliably ablate and remove solid material from any other hollow bodies, without parts of the solid bodies being distributed over the immediate working area. The invention also presents a method which enables reliable and simple removal, in particular of thrombi, from blood vessels.

According to the invention, this is achieved with the system and devices since the working head of the reducing catheter has a sleeve-shaped stator and a rotor which is arranged centrally therein and is rotatable relative to the stator, said stator being provided over its circumference with at least one lateral inlet opening, and said rotor being connected to a drive unit and feed screw or being formed in one piece, the at least one lateral inlet opening in the stator being advantageously formed as at least two circular holes arranged axially in succession in relation to the longitudinal axis of the reducing catheter.

The production of the substantially circular holes may be made using conventional tools, such as drills, milling cutters, etc. Circular holes can also be produced economically by punching, erosion, or water jet cutting. The edges which define the holes form shearing edges, on which aspirated material is comminuted. Two shearing edges running arcuately, viewed in the longitudinal direction of the working head, are formed per hole. Accordingly, four shearing edges are provided with two holes, six shearing edges are provided with three holes, etc. Advantageously with this form of the at least one lateral inlet opening, the working head of the reducing catheter cannot get caught in the sheathing catheter during the reducing process. At the same time, the shearing edges of the inlet opening ensure a cutting function of the reducing catheter so that the deposits reduced by the reducing catheter are fragmented or comminuted in such a way that a high reduction capacity is provided without the risk of the flexible sleeve becoming blocked when the fragmented material of the deposits is sucked up through the flexible sleeve.

Owing to the combination according to the invention with the sheathing catheter, the risk of individual particles of the thrombus being washed away by the circulation or flow of blood to more distant and sometimes inaccessible locations can be virtually excluded. Such particles trapped in the funnel-shaped end piece of the sheathing catheter can then also be removed from the end piece by means of the reducing catheter itself.

Whereas the stent-like end piece of the sheathing catheter thus previously had the function of catching and safekeeping, it is now employed as a system barrier against the washing away of particles in a novel combination with the reducing catheter. The end piece of the sheathing catheter increases reliability, and is no longer used to actually discharge the material to be discharged. A completely new use of the end piece, the material of which is known per se, and a new, much improved and more reliable treatment of the vessel occlusions are provided. The treatment system with cooperation of the two catheters thus achieves optimal results when removing material from hollow spaces.

In one version of the system, the sheathing catheter has a central duct, through which the reducing catheter can be inserted until the working head of the reducing catheter in the reducing state projects as far as the region of the funnel-shaped end piece. With this arrangement, the sheathing catheter and the reducing catheter are thus inserted into the hollow body from the same side, preferably against the blood flow. The reducing catheter likewise initially removes the thrombus by advancing the reducing catheter. With the subsequent withdrawal, the funnel-shaped end piece can be cleared out by means of the reducing catheter and the particles trapped therein can be removed. An advantage of this version is that the patient only has to be opened at one location.

Of course, with this design and with this use of the invention, the reducing catheter can also be positioned relatively far into narrow vessels. Merely the inner diameter of the vessel defines the diameter of the reducing catheter, which may be formed so as to be relatively small, however.

A particularly expedient embodiment has the circumferences of the holes of the at least one lateral inlet opening in the stator overlapping. For example, with two holes having overlapping circumferences, an approximately eight-shaped inlet opening is formed. This shape is advantageous for the cooperation with the funnel-shaped end piece, since the end piece of the sheathing catheter is thus additionally largely prevented from catching on the working head of the reducing catheter.

The holes are advantageously interconnected by a slit running in the axial direction and arranged substantially central to the holes. Such a slit prevents the formation of sharp teeth, which may be formed with holes having partly overlapping circumferences. In addition, further shearing edges are formed by the slit, said edges cooperating advantageously during the fragmenting or comminuting of the material aspirated by the reducing catheter.

The slit expediently extends towards the proximal end of the reducing catheter, beyond the holes. A duct which is narrower than the diameter of the holes is thus formed in the extension of the holes. Particularly tough parts of a thrombus, which cannot be sheared off in the region of the holes, are drawn into this duct and are sheared off at the proximal end of the duct at the latest. The shearing edges created additionally by this slit formation advantageously assist the fragmenting of the material aspirated by the reducing catheter. It is again stressed here that the discharge through the flexible sleeve of the reducing catheter is advantageously ensured by a sufficient comminution or fragmenting of the material reduced and aspirated by the working head, and that complications, which may occur during a surgical procedure as a result of a blocked suction duct, are largely excluded.

Two approximately diametrically opposed lateral inlet openings are advantageously provided on the stator of the reducing catheter. Two diametrically opposed inlet openings provide a uniform distribution of force during the reducing process and also provide a greater reduction capacity with a corresponding capacity of the feed screw. Furthermore, a multiplicity of shearing edges are available on the stator and ensure a sufficient fragmentation of the material aspirated by the working head. The mutually opposed lateral inlet openings are particularly advantageously arranged in a mirror image, thus ensuring a more uniform distribution of force during the reducing process and therefore improved reduction capacity.

The size of the thrombi to be removed from a blood vessel can vary very widely. It has therefore proven to be advantageous if the outer diameter of the stator of the working head is gradated so that it tapers towards its free distal end. With the tapered section at the distal end of the stator, a type of "core hole" is first produced in the thrombus and is then "drilled out" by the subsequent section of enlarged diameter. This new form of the stator enables a very high reduction capacity and thus leads to shortened treatment times for the patients.

The stent-like end piece expediently has a screen structure or lattice structure in the expanded state of the end piece. For example, this structure may exist in the form of a fabric made of a textile or metal material. As has already been mentioned, the purpose of the funnel-shaped end piece of the sheathing catheter is to catch from the blood flow any washed away particles of the thrombus. For this reason, a funnel-shaped end piece made of liquid-permeable material is preferred, whereby the blood flow is only restricted, but is not stopped completely, when the end piece is expanded.

To insert the sheathing catheter into the hollow body, the end piece is advantageously tapered towards the outer diameter of the sheathing catheter. If the end piece has reached its position after insertion into the hollow body, the end piece is expanded again, advantageously conically. The end piece can therefore advantageously be expanded in an umbrella-like manner.

With sufficient resilience or biasing of the material used for the end piece, the end piece can fold out automatically as soon as the end piece is positioned in the desired position. The end piece is advantageously radially expandable by means of an inflatable balloon, by means of a self-expanding mechanism, or by means of the reducing catheter. These assisting measures allow the end piece to fold out or expand, even if there is high resistance against the folding out of the end piece. Any technique which results in the positioned end piece being opened so that the vessel or hollow body (for example a stent) is closed in a particle-tight (not liquid-tight) manner may be used to form the end piece of the sheathing catheter. In particular, self-expanding lattice grids can be used for this purpose.

The working head of the reducing catheter preferably has an additional rotor element which rotates relative to the stator. A reducing catheter of this type is known under the trade name Rotarex® (applicant's trademark) and makes it possible to break up and reduce harder occlusions. The additional rotor element may be arranged on the inner face of the stator for example, in order to preserve the walls of the hollow body when the occlusions are broken up and reduced. Alternatively, the additional rotor element rotating in relation to the stator may be arranged on the outer face of the stator.

The edges of the holes are preferably formed as cutting edges, thus ensuring improved fragmenting of the material aspirated by the reducing catheter. The cutting edges are advantageously formed by sharp edges which are arranged on the stator of the working head, facing the feed screw. The cutting edges may also have a structured course, for example an undulating and/or zigzagged course.

When the additional rotor element is arranged on the inner face of the stator, this new form of the stator of the reducing catheter may also advantageously be used independently of the sheathing catheter, which is why this is also considered innovative.

An advantageous method according to the invention for removing material from inside hollow bodies, in particular for removing thrombi and emboli from blood vessels, also referred to as occlusion removal, includes inserting at least one guide wire into the hollow body and, before the reducing catheter is inserted, inserting a sheathing catheter, which is designed according to the above-mentioned embodiments, along the inserted guide wire until in front of the material to be removed and occluding the cross-section of the hollow body by means of the sheathing catheter, at least in part, the material to be removed being reduced by a reducing catheter, which is designed according to the above-mentioned embodiments, aspirated thereby and suctioned off through the flexible sleeve. This method allows removal of the deposit located in the hollow body without parts of the reduced material being deposited by the blood flow at more distant locations in the hollow body, which could lead to new constrictions or occlusions of the hollow body at these locations.

The sheathing catheter is expediently inserted first into the hollow body until in front of the material to be removed, and the hollow body is closed, at least in part, by radially expanding the end piece connected to the distal end of the sheathing catheter. The reducing catheter is then inserted into the hollow body from the side opposite the sheathing catheter until in front of the material to be removed, and the material to be removed is then aspirated into the at least one inlet opening in the stator with rotation of the feed screw, and is fragmented and then extracted through the flexible sleeve.

The sheathing catheter is preferably inserted into the hollow body against the direction of blood flow. When the material to be removed is reduced by the reducing catheter, detached material transported by the blood flow is caught and collected in the end piece of the sheathing catheter. Once the deposit in the hollow body has been removed, the expanded end piece of the sheathing catheter can be cleared out by means of the reducing catheter, that is to say relieved of material of the reduced deposit collected in the end piece. The end piece of the sheathing catheter is then advantageously folded together and the sheathing catheter and reducing catheter are removed from the hollow body in opposite directions.

In a further method, material deposited on a filter already arranged temporarily or permanently in the hollow body is cleared out by the reducing catheter. In known applications, a filter is positioned in the hollow body and closes the hollow body in a liquid-permeable, but particle-tight manner. This filter can be arranged in the hollow body temporarily, for example before or during surgical intervention, or permanently, that is to say over a relatively long period of time. In order to ensure the flow of blood through the filter arranged temporarily or permanently in the hollow body, said filter either has to be removed, wherein material collected in this filter may spread in the hollow body and therefore in the blood flow during the removal process, or cleared out by means of a reducing catheter. In the latter case, the device according to the invention is advantageously used. For example, the sheathing catheter is first advanced, advantageously against the blood flow or counter to the blood flow, until in front of the filter arranged temporarily or permanently in the hollow body, and the end piece of the sheathing catheter is expanded to close the hollow body at least in part. The reducing catheter is then inserted into the hollow body from the other side and the filter arranged temporarily or permanently in the hollow body is cleared out. Any material from the filter arranged temporarily or permanently in the hollow body entrained by the blood flow is caught in the expanded end piece of the sheathing catheter and can likewise be removed from the hollow body when the sheathing catheter is removed from the hollow body.

A further alternative advantageous method consists in, again, first inserting the sheathing catheter into the hollow body until in front of the material to be removed, and closing the hollow body, at least in part, by radially expanding the end piece. The reducing catheter is then inserted into the hollow body coaxially through a central duct through the sheathing catheter until in front of the material to be removed, and the material to be removed is then aspirated into the at least one inlet opening with rotation of the feed screw, and is fragmented and then extracted through the flexible sleeve. In this method the sheathing catheter and the reducing catheter are preferably introduced into the hollow body, and therefore into the body, at the same location so that only one insertion opening, for example in the patient's body, has to be created.

A common guide wire is expediently first inserted into the hollow body and then both the reducing catheter and the sheathing catheter are inserted into the hollow body via the common guide wire, either together or staggered over time, from one side or opposite one another, that is to say from two sides. The guide wire is inserted beforehand into the hollow body, for example with X-ray assistance, and guides the sheathing catheter and the reducing catheter during their insertion into the hollow body. The common guide wire ensures that the reducing catheter and the sheathing catheter meet one another. The reducing catheter and the sheathing catheter can therefore cooperate in an optimal manner, avoiding the risk of abandoning a blood vessel.

In an alternative method step, a first guide wire for the sheathing catheter is inserted into the hollow body and a second guide wire for the reducing catheter is inserted into the hollow body against the direction of insertion of the first guide wire. The sheathing catheter is positioned in the hollow body at the desired location via the first guide wire. The first guide wire is then withdrawn, at least in part, and the second guide wire is then introduced into the sheathing catheter, at least over a region thereof, and the reducing catheter is then reliably inserted in the hollow body along the second guide wire in the direction of the sheathing catheter. The guide wires normally used in such methods have a flexible end, which makes it easier to find the hollow body in question, for example if there are branchings. It is therefore sometimes difficult to insert the sheathing catheter and/or the reducing catheter into the hollow body via this flexible end of the guide wire. As a result of the insertion of the second guide wire into the sheathing catheter, at least over a region thereof, it is ensured in a further advantageous manner that the reducing catheter and the sheathing catheter meet one another and that the reducing catheter and the sheathing catheter can therefore cooperate with one another in an optimal manner.

The end piece connected to the proximal end of the sheathing catheter is preferably radially expanded by means of an inflatable balloon, by means of a self-expanding mechanism, or by the reducing catheter, which ensures that the hollow body is occluded, at least in part, by the expanded end piece.

Further explanation of versions of the invention is found in the figures and in the detailed description. The appended list of reference labels forms part of the disclosure.

The invention will be explained in greater detail symbolically and by way of example on the basis of the included figures of drawings. The figures are described coherently and comprehensively. Like reference labels denote like components in the several views.

Figure 1:
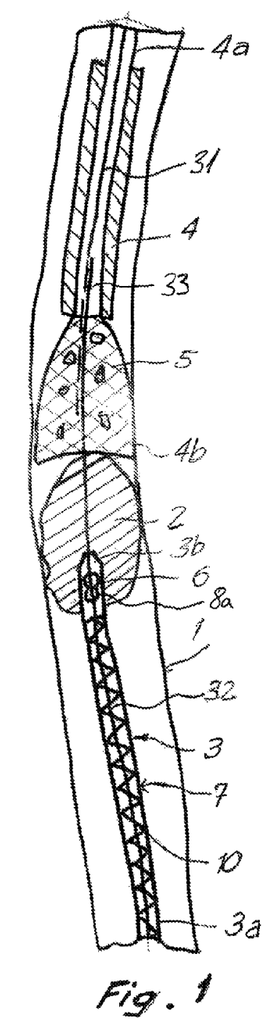
FIG. 1 shows a blood vessel blocked by a thrombus, with a reducing catheter and sheathing catheter inserted into the blood vessel from different directions, at the start of the treatment.
Figure 2:
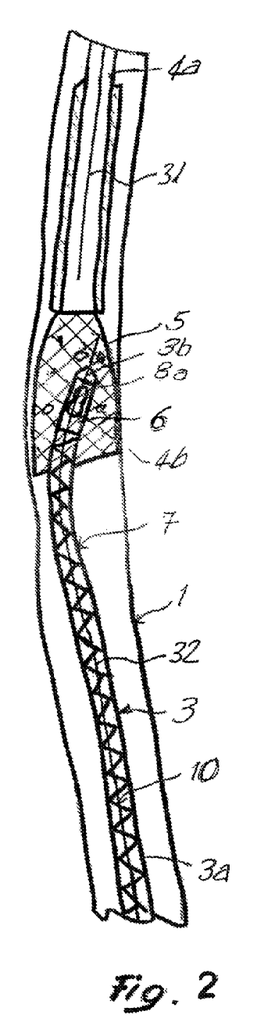
FIG. 2 shows the blood vessel according to FIG. 1, after removal of the thrombus.
Figure 3:
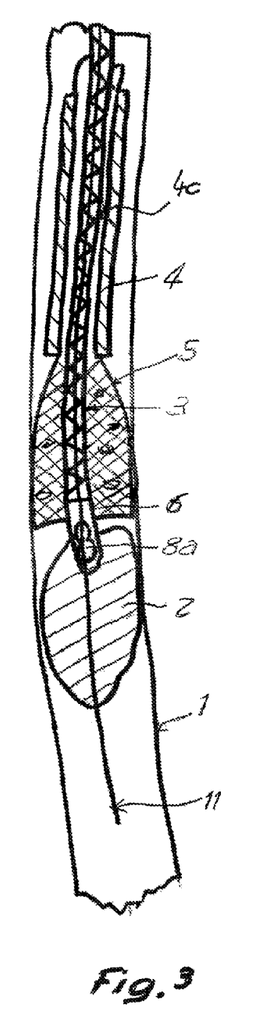
FIG. 3 shows a variant of the method illustrated in FIGS. 1 and 2.

FIGS. 1 to 3 show schematic views of a hollow body 1, for example a vein or artery, in longitudinal section. A deposit impeding the circulation of blood is located in the hollow body 1. For example, this may be a thrombus 2 or an embolus, the material of which has to be removed so that the blood circulation functions correctly again and the body organs are supplied sufficiently with the necessary substances.

A device for removing and extracting a thrombus 2 from inside the hollow body 1 is illustrated in each of FIGS. 1 and 2. The device comprises a reducing catheter 3 which can be inserted into the hollow body 1, and a sheathing catheter 4, which can likewise be inserted into the same hollow body 1. The sheathing catheter 4 has a proximal end 4a and a distal end 4b. The distal end 4b of the sheathing catheter 4 is connected to a radially deformable, funnel-shaped end piece 5 made of liquid-permeable material.

The reducing catheter 3 likewise has a proximal end 3a and a distal end 3b. A working head 6 is located at the distal end 3b. The working head 6 is connected to a flexible, tubular sleeve 7. The working head 6 of the reducing catheter 3 has an outer diameter which is smaller than the inner diameter of the widened end piece 5 for insertion into the region of the funnel-shaped end piece 5 of the sheathing catheter 4. As will be described in detail hereinafter in conjunction with FIGS. 4 to 10, the working head 6 of the reducing catheter 3 has a sleeve-shaped stator 8, and a rotor 9 which is arranged centrally therein and is rotatable relative to the stator 8, said stator 8 being provided over its circumference with at least one lateral inlet opening 8a.

Figure 12A:
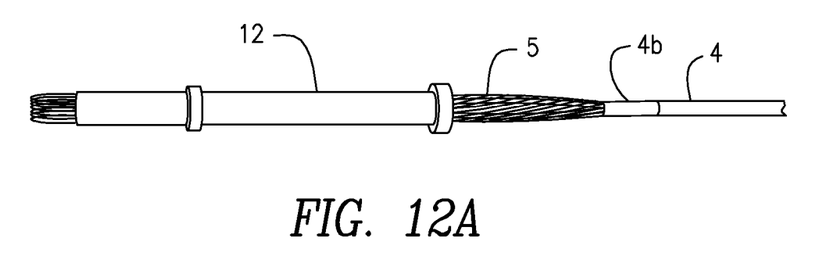
FIGS. 12A to 12B show sheathing catheter distal end with end piece and end-piece sleeve; and, FIG. 13 shows a reducing catheter partial assembly with extended end piece and with an end-piece sleeve actuator.
Figure 12B:
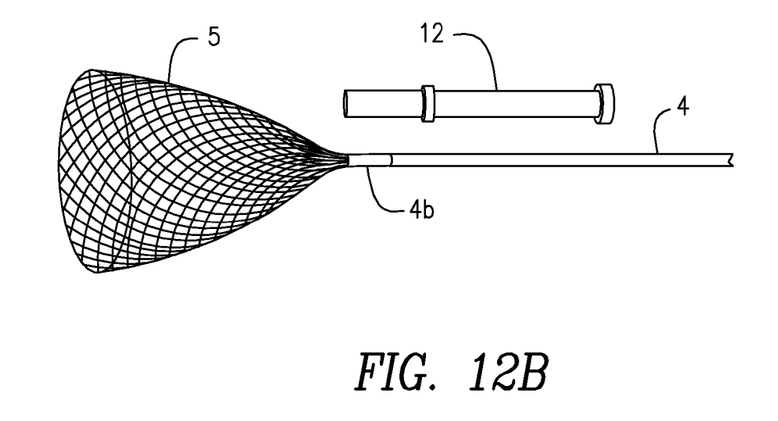
Figure 13:
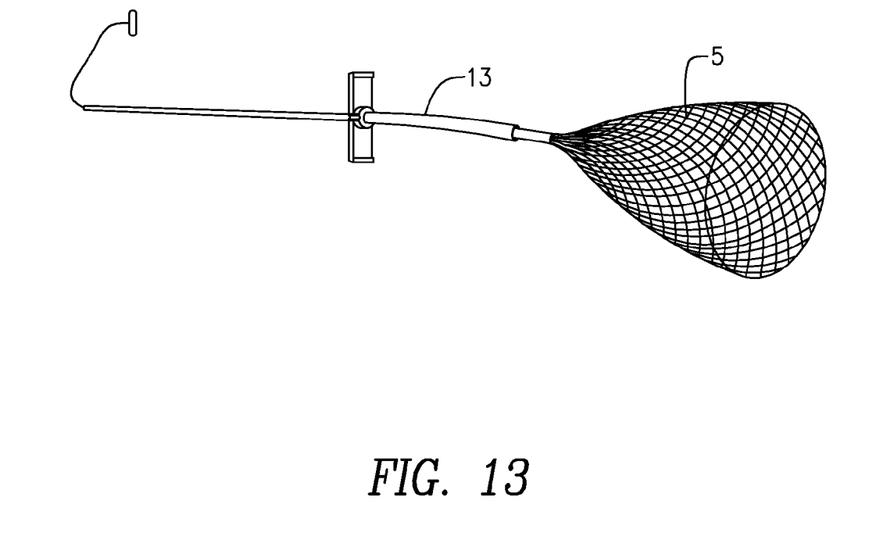

In the method illustrated in FIGS. 1 and 2, a first guide wire 31 is first inserted into the hollow body 1 until approximately at the thrombus 2 (see dashed end of the first guide wire 31). The sheathing catheter 4 is then likewise inserted into the hollow body 1 via the first guide wire 31 from the same side, and is advanced until immediately in front of the thrombus 2 to be removed. During the insertion process, the diameter of the end piece 5 is compressed, for example by a destructible sleeve. FIG. 12A depicts the end piece 5 in a folded, compressed state within an end-piece sleeve 12. In a related view, FIG. 12B depicts the unfolded, expanded end piece as unrestrained by end-piece sleeve 12. A sleeve 12 of this type may also be actuated by an actuator that permits it to be selectively controllably positioned relative to the end piece 5. As may be understood, the sleeve is pulled back for expansion of the end piece and pushed forward for collapsing the end piece. FIG. 13 depicts a version of the sleeve actuator 13 for the sleeve 12. If the desired position of the end piece 5 of the sheathing catheter 4 is reached, the sleeve is then removed and the end piece 5 can unfold in an umbrella-like manner as a result of its own resilience. Alternatively, the end piece 5 is radially expanded by additional external tools, for example by means of an inflatable balloon, by means of a self-expanding mechanism, or by the reducing catheter. The hollow body 1 is closed, at least in part, by the end piece 5 of the sheathing catheter 4. As a result of the liquid-permeable material of the end piece 5, the blood can still flow through the hollow body 1, however. Only the solid components or particles contained in the blood flow are filtered out by the end piece 5 of the sheathing catheter 4.

A second guide wire 32 is inserted into the hollow body 1 from the side of the thrombus 2 opposite the sheathing catheter 4, either once the sheathing catheter 4 has been arranged correctly in the predefined position, or before the sheathing catheter 4 has been positioned, and is fed through the thrombus 2. The first guide wire 31 is then withdrawn slightly and the second guide wire 32 is then advanced further so that the free end 33 thereof penetrates into the sheathing catheter 4 over a region thereof. The reducing catheter 3 is then introduced into the hollow body 1 along the second guide wire 32 from the side opposite the sheathing catheter 4.

Figure 4:
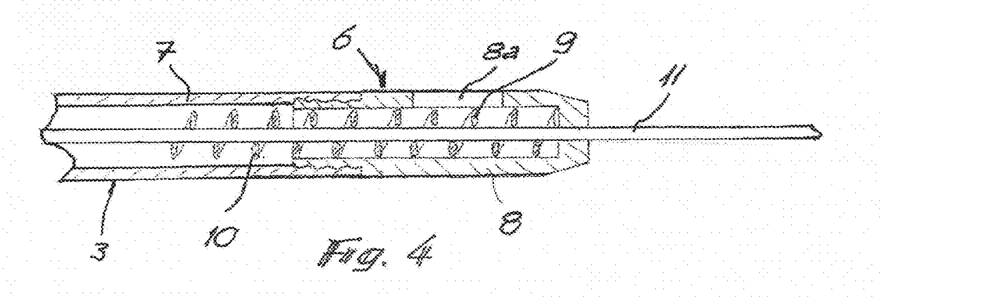
FIG. 4 shows an enlarged, longitudinal sectional view of the reducing catheter which can be seen from FIGS. 1 to 3.

As can be seen in particular from FIG. 4, the working head 6 of the reducing catheter 3 version depicted therein comprises a sleeve-shaped stator 8 and a feed screw 10 which is mounted coaxially therein and is connected either integrally or in a coupled manner to a rotor 9, likewise acting as a feed screw. In the present example the distal end portion of the feed screw 10 rotating in the stator 8 forms the rotor 9. The stator 8 is provided with at least one lateral inlet opening 8a and, at its distal end, has a section tapering towards the free end. The stator 8 is connected at its proximal end to a tubular, flexible sleeve 7.

As shown in FIG. 1, the thrombus 2 is then reduced by the working head 6 of the reducing catheter 3. Parts of the thrombus 2 are drawn through the inlet opening 8a in the stator 8 into the inside of the working head 6 as a result of a vacuum produced by the rotation of the feed screw 10, and are sheared (fragmented or comminuted) on the edges of the inlet opening 8a by the relative rotation between the rotor 9 and stator 8, and discharged through the flexible sleeve 7 via the feed screw 10. The sheathing catheter 4 flexes continuously at its end piece 5 during the reducing process so that the hollow body 1 is reliably occluded.

Any components of the thrombus 2 which become detached and are not sucked up into the working head 6 of the reducing catheter 3, these components being transported further by the blood stream or blood flow, are caught in the expanded funnel-shaped end piece 5 of the sheathing catheter 4. Once the entire thrombus 2 has been removed by means of the reducing catheter 3, the funnel-shaped end piece 5 of the sheathing catheter 4 can also be cleared out by further advancing the reducing catheter 3, and relieved of the particles trapped therein. This can be seen clearly from FIG. 2. The second guide wire 32 can be withdrawn slightly to clear out the end piece 5 of the sheathing catheter 4, and therefore the working head 6 of the reducing catheter 3 is movable freely within the end piece 5 of the sheathing catheter 4. The reducing catheter 3 and the second guide wire 32 as well as the sheathing catheter 4 and the first guide wire 31 are then extracted from the hollow body 1 in opposite directions and removed therefrom.

In the method illustrated in FIG. 3, in contrast to the method according to the illustrations in FIGS. 1 and 2, the reducing catheter 3 and the sheathing catheter 4 are inserted into the hollow body 1 from the same side. The sheathing catheter 4 is first inserted into the hollow body along a previously inserted guide wire 11 until in front of the thrombus 2 to be removed. The funnel-shaped end piece 5 of the sheathing catheter 4 is then radially expanded so that the hollow body 1 is closed, at least in part. Once the end piece 5 is arranged in position, the reducing catheter 3 is inserted through a central duct 4c in the sheathing catheter 4 and the reduction of the thrombus 2 is begun from this side. Any particles which become detached and are washed away by the blood flow are caught by the funnel-shaped end piece 5 of the sheathing catheter 4, similarly to the methods described in conjunction with FIGS. 1 and 2. When the reducing catheter 3 is then withdrawn through the sheathing catheter 4, the funnel-shaped end piece 5 of the sheathing catheter 4 can be cleared out and any particles located therein can be removed. With this method, the reducing catheter 3 and the sheathing catheter 4 are guided on a common guide wire 11.

In a variant, in which the reducing catheter is also used at the same time to expand the end piece of the sheathing catheter, the sheathing catheter is shaped in the radially inward region in such a way that it is narrower than the outer diameter of the reducing catheter. If the reducing catheter is then pushed forwards axially with gentle pressure, it expands the end piece of the sheathing catheter.

Figure 11:
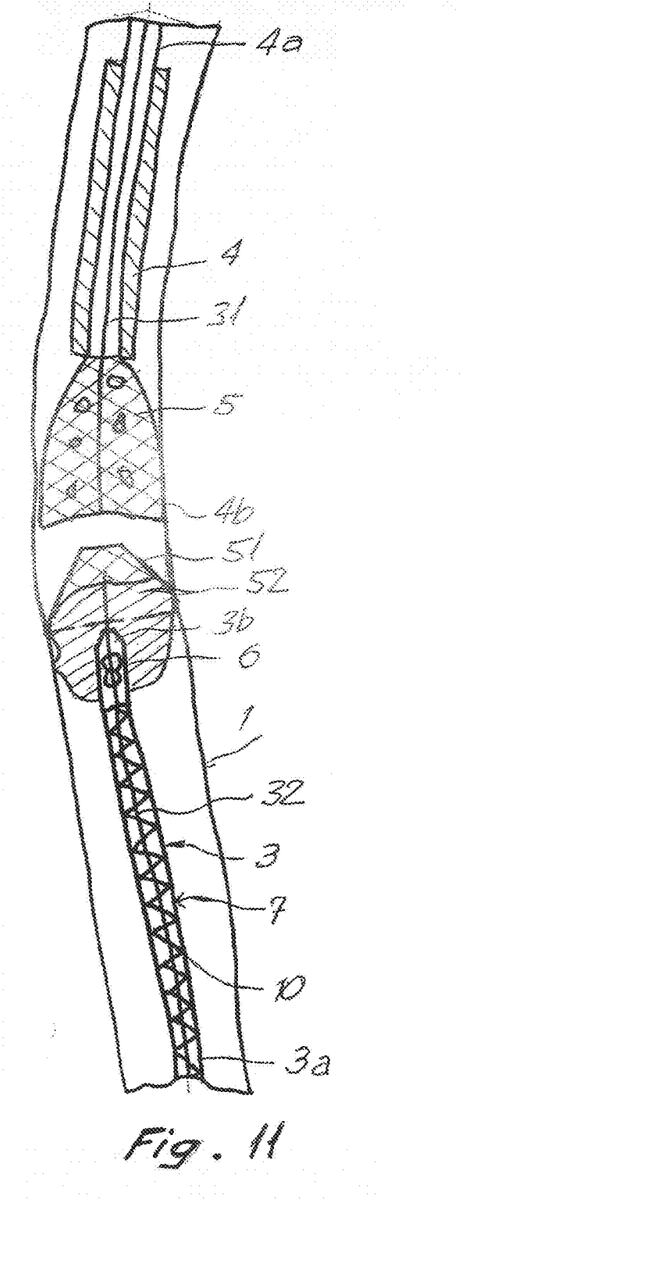
FIG. 11 depicts a further variant of the method illustrated in FIGS. 1 and 2.

In the method illustrated in FIG. 11, material 52 is cleared out from a filter 51, which is already arranged temporarily or permanently in the hollow body 1, by means of the device comprising a sheathing catheter 4 and a reducing catheter 3. The method for positioning the sheathing catheter 4 and arranging the reducing catheter 3 basically corresponds to the methods described in conjunction with FIGS. 1 and 2. When the material located in the filter 51 is removed, any particles transported by the blood stream are caught in the expanded end piece 5 of the sheathing catheter 4.

Figure 5A:
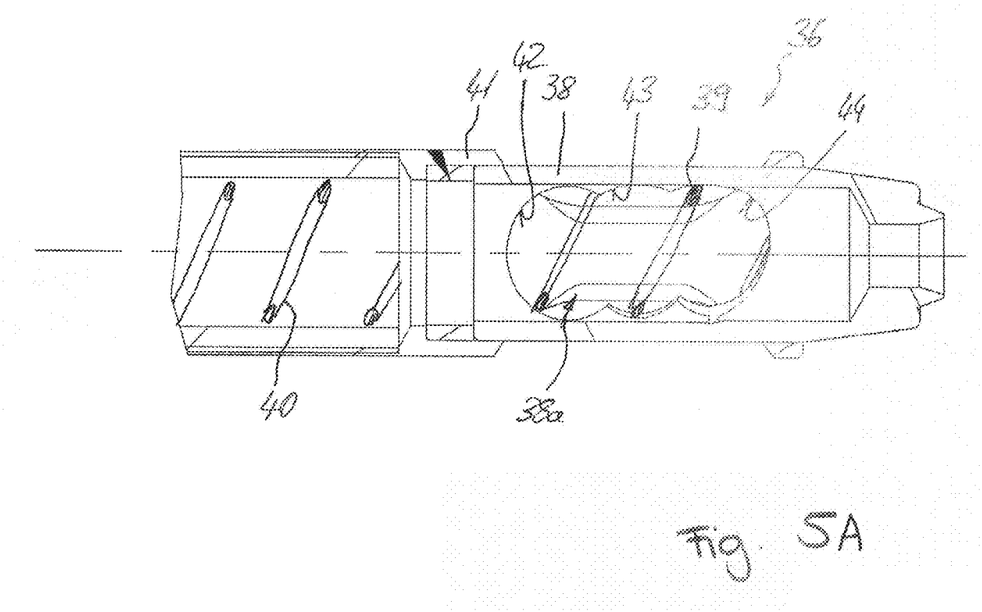
FIGS. 5A to 5B show longitudinal sectional views of variants of the reducing catheter.
Figure 5B:
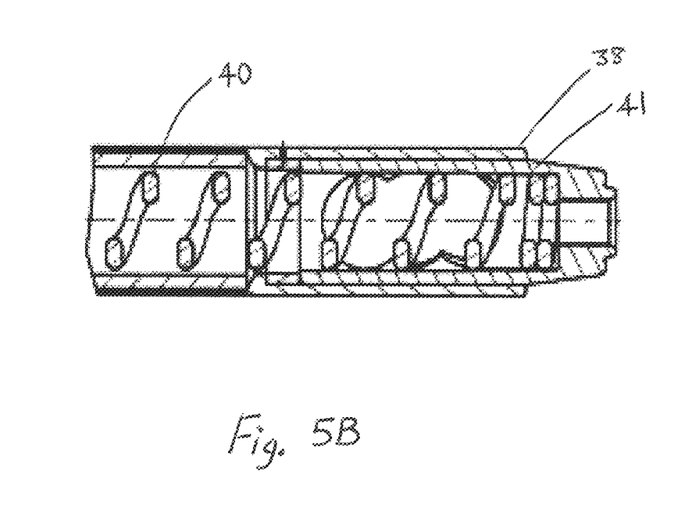
Figure 6:
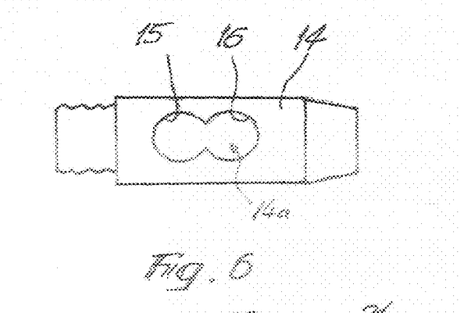
FIGS. 6 to 10 show different versions of the stator arranged on the distal end of the reducing catheter.

Variants of a working head 36 of a reducing catheter 3 are illustrated in FIGS. 5A-5B. Considering FIG. 5A, besides the stator 38, the working head 36 also comprises an additional, in this case external, rotor element 41. Examples of this type of rotor (external) may be found in Applicant's prior U.S. Pat. No. 5,876,414 and U.S. Pat. No. 5,873,882, the respective entireties of which are incorporated herein by reference, each as to all of its parts in full. The stator 38 also has a plurality of lateral inlet openings 38a which are each formed by three circular holes 42, 43 and 44 arranged axially in succession in relation to the longitudinal axis of the reducing catheter 3. The circumferences of the holes 42, 43 and 44 overlap. As a result of the design of the holes 42, 43 and 44, each inlet opening 38a has six shearing edges, which are advantageously formed as cutting edges.

In a related variant which is illustrated in FIG. 5B, the additional rotor element 41 is provided on the inner face of the stator 38.

FIGS. 6-10 shows different versions of the stator. With the stator 14 according to FIG. 6, two circular holes 15, 16 are arranged axially in succession in such a way that the circumferences thereof overlap in part. This lateral inlet opening 14a thus has the shape of a figure eight and has four shearing edges.

Figure 7:
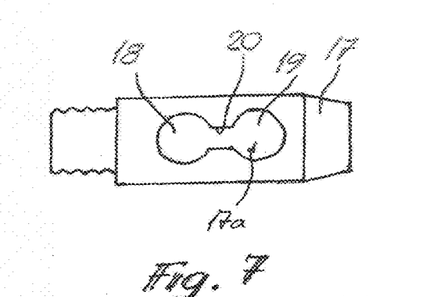

With the stator 17 which can be seen from FIG. 7, two holes 18, 19 are likewise arranged axially in succession and form the lateral inlet opening 17a. In this case the circumferences of the holes do not overlap, however. The two holes 18, 19 are interconnected by a slit 20 extending in the axial direction.

Figure 8:
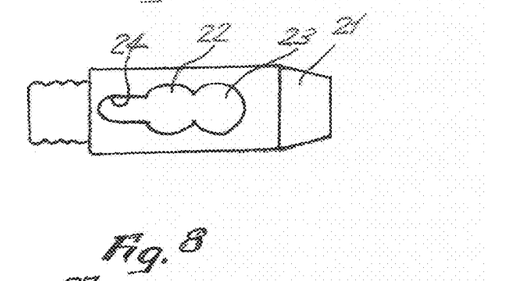

The stator 21 which can be seen from FIG. 8 differs from the embodiment according to FIG. 7 in that a slit 24 extends axially beyond the two holes 22, 23 towards the proximal end. The slit 24 and the two holes 22, 23 form the lateral inlet opening 21a. This slit 24 is particularly advantageous in the case of very tough and fibrous material to be ablated, since it provides good shearing and therefore fragmenting of the aspirated material as a result of the additional shearing edges available.

Figure 9:
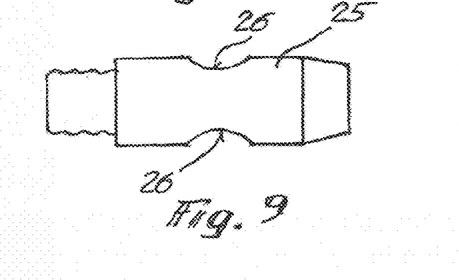

As the stator 25 which can be seen from FIG. 9 shows, two approximately diametrically opposed inlet openings 26 may also be provided and are advantageously arranged in a mirror image.

Figure 10:
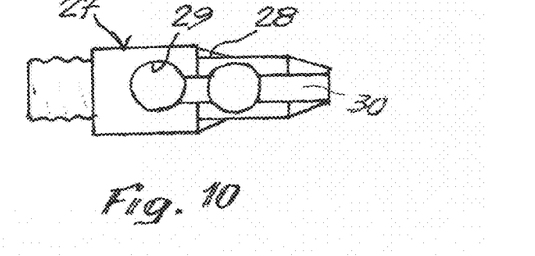

The stator 27 which can be seen from FIG. 10 differs from the embodiments illustrated in FIGS. 5 to 9 in that the diameter of said stator is gradated towards its distal end. The reduced diameter of the stator 27 at its distal end enables easier penetration of the reducing catheter 3 into the material to be removed.

The configurations of the lateral inlet openings on the stator which can be seen from FIGS. 5 to 10 are particularly expedient in cooperation with the funnel-shaped end piece 5 of the sheathing catheter 4. The stator can thus be largely prevented from catching or becoming stuck in the material of the end piece 5.

| List of reference labels | |
|---|---|
| 1 | hollow body |
| 2 | thrombus |
| 3 | reducing catheter |
| 3a | proximal end of 3 |
| 3b | distal end of 3 |
| 4 | sheathing catheter |
| 4a | proximal end of 4 |
| 4b | distal end of 4 |
| 4c | central duct of 4 |
| 5 | end piece |
| 6 | working head |
| 7 | flexible sleeve |
| 8 | stator |
| 8a | inlet opening |
| 9 | rotor |
| 10 | feed screw |
| 11 | guide wire |
| 12 | end-piece sleeve |
| 13 | sleeve actuator |
| 14 | stator |
| 14a | inlet opening |
| 15 | hole |
| 16 | hole |
| 17 | stator |
| 17a | inlet opening |
| 18 | hole |
| 19 | hole |
| 20 | slit |
| 21 | stator |
| 21a | inlet opening |
| 22 | hole |
| 23 | hole |
| 24 | slit |
| 25 | stator |
| 26 | inlet opening |
| 27 | stator |
| 28 | step |
| 29 | hole |
| 30 | slit |
| 31 | 1st guide wire |
| 32 | 2nd guide wire |
| 33 | free end of 32 |
| 38 | stator |
| 38a | inlet opening |
| 39 | rotor |
| 40 | feed screw |
| 41 | rotor element |
| 42 | hole |
| 43 | hole |
| 44 | hole |
| 51 | filter |
| 52 | material |

What is claimed is:

1. A process of aspirating, fragmenting and extracting removable deposit material from a hollow body, comprising the steps of:
   providing a proximal end of a reducing catheter;
   providing a distal end of the reducing catheter;
   providing a working head at the distal end;
   providing a stator at the working head;
   providing a rotatably-mounted rotor rotatable relative the stator;
   providing a first guide wire for guiding the working head;
   providing a screw operatively connected to the rotor and disposed surrounding at least a portion of the guide wire;
   providing a flexible sleeve surrounding the screw and connected to the stator;
   providing, at the proximal end of the reducing catheter, a drive unit for driving the screw;
   providing at least one lateral inlet opening on the stator's circumference;
   inserting the reducing catheter into the hollow body in a first direction;
   providing a sheathing catheter;
   providing a second guide wire for guiding the sheathing catheter;
   inserting the second guide wire into the hollow body in a second direction opposite to the first direction;
   withdrawing, at least in part, the second guide wire;
   inserting the sheathing catheter into the hollow body before said step of inserting the reducing catheter into the hollow body in the first direction;
   introducing the first guide wire into the sheathing catheter end, at least over a region thereof, before said step of guiding the reducing catheter on the first guide wire;
   guiding the reducing catheter on the first guide wire;
   forcing deposit material into the at least one lateral opening and cutting this deposit material between peripheral edges of the at least one lateral opening and of the stator;
   positioning the inserted sheathing catheter in front of deposit material to be removed; and,
   occluding, with an expandable end piece of the sheathing catheter, a cross section of the hollow body, at least in part.

2. A process of aspirating, fragmenting and extracting removable deposit material from a hollow body as claimed in claim 1, further comprising the steps of:
   said step of inserting the sheathing catheter into the hollow body is made in the second direction opposite to the first direction of the reducing catheter insertion;
   said step of inserting the reducing catheter into the hollow body in a first direction is followed by a step of positioning said reducing catheter at rear of the deposit material to be removed;
   aspirating deposit material into the at least one lateral opening with rotation of the screw; and,
   extracting cut deposit material through the flexible sleeve.

3. A process of aspirating, fragmenting and extracting removable deposit material from a hollow body as claimed in claim 1, further comprising the step of:
   operating the reducing catheter to clear out deposit material from a filter arranged in the hollow body.

4. The process of aspirating, fragmenting and extracting removable deposit material from a hollow body as claimed in claim 1, wherein:
   said step of inserting the sheathing catheter into the hollow body is made in a second direction opposite to the first direction; and,
   said step of positioning the inserted sheathing catheter is followed by said step of inserting the reducing catheter into the hollow body in the first direction.

5. A process of aspirating, fragmenting and extracting removable deposit material from a hollow body as claimed in claim 1, further comprising the step of:
   radially expanding the end piece by the reducing catheter.

* * * * *